United States Patent
Zhu

(10) Patent No.: US 10,849,655 B2
(45) Date of Patent: Dec. 1, 2020

(54) TROCAR SEAL MEMBRANE AND ASSEMBLY COMPRISING NORMAL AND REVERSE CONCAVE CHANNELS

(71) Applicant: 5RMED TECHNOLOGY (CHENGDU) CO., LTD., Chengdu (CN)

(72) Inventor: Moshu Zhu, Chengdu (CN)

(*) Notice: Subject to any disclaimer, the term of this patent is extended or adjusted under 35 U.S.C. 154(b) by 83 days.

(21) Appl. No.: 16/243,514

(22) Filed: Jan. 9, 2019

(65) Prior Publication Data

US 2019/0142463 A1 May 16, 2019

Related U.S. Application Data

(63) Continuation of application No. PCT/CN2017/093608, filed on Jul. 20, 2017.

(51) Int. Cl.
*A61B 17/34* (2006.01)
*A61M 39/06* (2006.01)
*A61B 17/00* (2006.01)

(52) U.S. Cl.
CPC ...... *A61B 17/3462* (2013.01); *A61B 17/3474* (2013.01); *A61B 17/3498* (2013.01);
(Continued)

(58) Field of Classification Search
CPC .............. A61B 17/3462; A61M 39/06; A61M 2039/0626; A61M 2039/0686;
(Continued)

(56) References Cited

U.S. PATENT DOCUMENTS

| 5,342,315 A | 8/1994 | Rowe et al. |
| 5,827,228 A | 10/1998 | Rowe |

(Continued)

FOREIGN PATENT DOCUMENTS

| CN | 101474089 A | 7/2009 |
| CN | 101478924 A | 7/2009 |

(Continued)

OTHER PUBLICATIONS

Internation Search Report of PCT/CN2017/093608, dated Aug. 29, 2017.

*Primary Examiner* — Emily L Schmidt
(74) *Attorney, Agent, or Firm* — Erson IP (Nelson IP)

(57) ABSTRACT

Disclosed is a trocar seal membrane and assembly including normal concave-channels and reverse concave-channels. The seal membrane includes a proximal opening, a distal aperture, and a sealing wall from the distal aperture extending to the proximal opening. The distal aperture formed by a sealing lip for accommodating the inserted instrument forms a gas-tight seal. The sealing wall includes a proximal surface and a distal surface. The sealing wall is a seamless sealing body with multiple normal concave-channels and multiple reverse concave-channels surrounding the sealing lip in an alternating manner. The normal concave-channels and reverse concave-channels has the functions of enlarging hoop circumference, reducing the wrapped-area, improving lubrication reliability, increasing the axial tensile stiffness, etc., thereby, the frictional resistance and the stick-slip can be greatly reduced.

15 Claims, 11 Drawing Sheets

(52) U.S. Cl.
CPC ... *A61M 39/06* (2013.01); *A61B 2017/00477* (2013.01); *A61B 2017/00862* (2013.01); *A61B 2017/3464* (2013.01)

(58) Field of Classification Search
CPC .. A61M 2039/0633; A61M 2039/0653; A61M 2039/0673; A61M 2039/064; A61M 2039/0646; A61M 39/0606
See application file for complete search history.

(56) References Cited

U.S. PATENT DOCUMENTS

| | | |
|---|---|---|
| 7,112,185 B2 | 9/2006 | Hart et al. |
| 7,591,802 B2 | 9/2009 | Johnson et al. |
| 7,789,861 B2 | 9/2010 | Franer |
| 7,842,014 B2 | 11/2010 | Schweitzer et al. |
| 2007/0051375 A1 | 3/2007 | Milliman |
| 2007/0255218 A1* | 11/2007 | Franer ............... A61B 17/3462 604/167.02 |
| 2011/0288483 A1 | 11/2011 | Zhou et al. |

FOREIGN PATENT DOCUMENTS

| | | |
|---|---|---|
| CN | 101480354 A | 7/2009 |
| CN | 204351906 U | 5/2015 |
| CN | 104873251 A | 9/2015 |
| CN | 105997205 A | 10/2016 |
| EP | 0994740 A1 | 4/2000 |

* cited by examiner

TROCAR SEAL MEMBRANE AND ASSEMBLY COMPRISING NORMAL AND REVERSE CONCAVE CHANNELS

CROSS-REFERENCE TO RELATED APPLICATIONS

This application is a continuation of International Patent Application No. PCT/CN2017/093608 with a filing date of Jul. 20, 2017, designating the United States, now pending, and further claims priority to Chinese Patent Application No. 201610625846.3 with a filing date of Aug. 2, 2016. The content of the aforementioned applications, including any intervening amendments thereto, are incorporated herein by reference.

TECHNICAL FIELD

The present invention relates to a minimally invasive surgical instrument, and in particular, to trocar sealing element.

BACKGROUND OF THE PRESENT INVENTION

A trocar is a surgical instrument, that is used to establish an artificial access in minimally invasive surgery (especially in rigid endoscopy). Trocars comprise in general a cannula and an obturator. The surgical use of trocars generally known as: first make the initial skin incision at the trocar insertion site, then insert the obturator into the cannula, and then together they facilitated penetration of the abdominal wall through incision into the body cavity. Once penetrated into the body cavity, the obturator is removed, and the cannula will be left as access for the instrument get in/out of the body cavity.

In rigid endoscopy surgery, it is usually necessary to establish and maintain a stable pneumoperitoneum for the sufficient surgical operation space. The cannula comprises a sleeve, an outer body, a seal membrane (also known as instrument seal) and a duck bill (also known as closure valve). Said cannula providing a channel for the instrumentation in/out of the body cavity, said outer body connecting the sleeve, the duck bill and the seal membrane into a sealing system; said duck bill normally not providing sealing for the inserted instrument, but automatically closing and forming a seal when the instrument is removed; said seal membrane accomplishing a gas-tight seal against the instrument when it is inserted.

In a typical endoscopic procedure, it is usually set up 4 trocars (access), i.e. 2 sets of small diameter cannula (normally 5 mm in diameter), and 2 sets of large diameter cannula (normally 10-12 mm in diameter). Instruments, in general passing through a small cannula are only for ancillary works; herein one large cannula as an endoscope channel, and the other large cannula as the main channel for surgeon to perform surgical procedures. Through said main channel thereof, 5 mm diameter instruments used in approximately 80% of the procedure, and said large cannula used in approximately 20% of the procedure; furthermore, 5 mm instruments and large diameter instruments need to be switched frequently. The small instruments are mostly used, so that the sealing reliability of which is more important. The large instruments are more preferably used in a critical stage of surgery (Such as vascular closure and tissue suturing), therein switching convenience and operational comfort are more important.

FIG. 1 and FIG. 2 depict atypical 12 mm diameter cannula 700. Said cannula 700 comprises a lower housing 710, an upper housing 720, a seal membrane 730 which sandwiched between the lower housing 710 and the upper housing 720, and a duckbill seal 750. Said lower housing 710 including center hole 713 defined by an elongated tube 711. Said upper housing 720 including the proximal hole 723 defined by the inner wall 721. Said membrane 730 including a proximal opening 732, a distal aperture 733, a sealing lip 734, a frustum sealing wall 735, a flange 736 and an outer floating portion 737. Said distal opening 733 formed by a sealing lip 734. Said sealing lip 734 defining a longitudinal axis 741, transverse plane 742 substantially perpendicular to said axis 741; define the angle between the rotary-generating line (or generatrix) of the frustum sealing wall 735 and the transverse plane 742 as a guide angle ANG1.

As illustrated in FIG. 1, when a 5 mm diameter instrument inserted, it is approximately considered that only hoop force generated by the deformation of the sealing lip 734, ensures a reliable seal for the instrument. It is nevertheless favorable to operate the instrument from various extreme angles in surgery. There's a lot space left for the 5 mm-instrument to move radially in the 12 mm diameter cannula, so that greater radial force would be taken by the sealing lip 734. Therefore, the sealing lip 734 should have sufficient hoop force for the inserted 5 mm diameter instrument to ensure its sealing reliability thereof.

As illustrated in FIG. 2, drawing a cylinder of Di (Di>5 mm) to cut the sealing wall 735 forms an intersecting line 738. It is easy to understand for those skilled in the art, when an Di diameter instrument is inserted, the strain (stress) of said sealing wall 735 in the area from the sealing lip 734 to the intersecting line 738 will be larger, so the area refer to as lip-adjacent area (or concentration stress area). While the strain (stress) of said sealing wall 735 from the intersecting line 738 to the flange 736 is small. However, the different diameter (Di value) makes the boundary range of the lip-adjacent area (or concentration stress area) change larger or smaller. For the convenience of quantification, it is defined when Di is designed as the maximum diameter of the surgical instrument passing through the seal membrane, the area from the sealing lip 734 to the intersection line 738 is the lip-adjacent area.

As illustrated in FIG. 3, when a large diameter instrument is inserted (e.g. 12.8 mm), the sealing lip 734 will expand to a suitable size to accommodate the inserted instrument; said sealing wall 735 is divided into two portions: a conical wall 735c and a cylindrical wall 735d; said cylindrical wall 735d wrapped around the outer surface of the instrument to form a wrapped area with a high concentration of stress. Defining the intersecting line of the conical wall 735c and the cylindrical wall 735d as intersecting line 738a. When the instrument is removed, said sealing wall 735 return to natural state, and said intersecting line 738a spring-back to a ring radius of Dx, defined as intersecting line 738b, (not shown in FIG.); said intersecting line 738b is a bending boundary line when inserting a large diameter instrument. The angle between the rotary generating line of said conical wall 735c and the transverse plane 742 defines as ANG2, ANG2>ANG1; that is, when the large-diameter instrument is inserted, said sealing wall 735 rotates and stretch around its intersection line of said flange 736. Defining the height of the cylindrical wall 735d as Ha, not a fixed value; the factors such as different size of said distal aperture, different size of said sealing lip, different thickness of said sealing wall, different said guide angle or different diameter of inserted instrument, make Ha different.

The instrument inserted into the sealing membrane and moved during surgical procedure, there is large frictional resistance between the wrapped area and the inserted instrument. Said large frictional resistance is normally easy to cause the seal inversion, poor comfort of performance, fatigue performance, even result in cannula insecurely fixed on the patient's abdominal wall etc., such that the performance of cannula assembly is affected.

Among the defects caused by the large frictional resistance, the seal inversion is one of the most serious problems that affecting the performance of the cannula. As illustrated in FIG. 4, when a large diameter instrument is removed, easily cause seal inversion. When inversion happened, said sealing wall 735 divided into a cylindrical wall 735e, a conical wall 735f, and a conical wall 735g; said cylindrical wall 735e wrapped around the outer surface of the instrument to form a wrapped area with a high concentration of stress. Defining the height of the cylindrical wall 735e to be Hb, normally Hb>Ha; that is, the frictional resistance when the instrument is removed greater than it when the instrument is inserted, this difference affects the surgeon's operating feeling and even make the surgeon confused. More seriously, the inversion of the seal membrane may stretch into the proximal hole 723, that is the seal membrane positioned between the instrument and the inner wall 721 gets completely jammed. Measures for preventing the seal inversion are respectively disclosed in U.S. Pat. Nos. 7,112,185 and 7,591,802, and those measures can effectively reduce the probability of inversion but not completely solve the problem.

The simplest way to reduce the frictional resistance is reducing the coefficient of friction between the two contacting surfaces with grease, but the reliability of this way is not good. During procedures, due to instruments long-term repeated scraping with the seal membrane and repeated switching, it is easy to erase the grease off and carried away, resulting in bad lubrication.

A protector assembly adjoined by a seal membrane is disclosed in U.S. Pat. No. 5,342,315. Said protector to permit the sharp edge of the instrument to pass through the opening in the seal membrane without causing damage to the seal membrane, and the surface friction coefficient of the protector assembly is smaller than the surface friction coefficient of the seal membrane, which results in less frictional drag, but the lip-adjacent area is normally not completely covered by the protector assembly.

A seal member with ribs is disclosed in U.S. Pat. No. 5,827,228, that is a plurality of spaced ribs provided to extend outwardly from center hole to reduce surface contact between the inserted instrument and the seal member, and thereby reducing the frictional resistance, a similar ribs which disclosed in EP0994740 also reducing surface contact and strengthen the tensile of the seal member oriented to axial.

A sealing element comprising a flexible wall closed annularly with the edges foldable in a wave-like manner is disclosed in U.S. Pat. No. 7,842,014, wherein the wall bears a wave-like sealing lip and is a wavy pleated seal body, in such manner it can enlarge hoop circumference, and reduce the hoop force to a certain extent.

Chinese invention application CN101480354A (currently rejected) discloses a seal member containing an easily deformable groove, wherein is characterized in that it has a plurality of easily deformable grooves on the conical surface of the seal member from the sealing lip; said the thickness of the deformable groove wall is much smaller than the thickness of the conical surface wall, primary take advantage of the elongation of the deformable groove to accommodate the inserted large diameter instrument.

Although, in the prior art many solutions for reducing the frictional resistance have been disclosed, these solutions basically only propose measures from one certain factor affecting frictional resistance, the effect of which is small or not obvious. Some modifications solved a certain defects may lead to cause another bug. Such as, reinforcing ribs on the seal membrane to reduce surface contact, meanwhile strengthen the tensile of the seal membrane; or a deformable groove with a thickness much smaller than that of a truncated conical surface can cause the deformable groove to be easily damaged; due to the adoption of said wave-like sealing lip which enlarge hoop circumference, the sealing reliability will be sacrificed when a 5 mm diameter instrument is inserted, if the wave-like sealing lip is used but without enlarge hoop circumference, the wave-like sealing lip will lose its improvement effect. In summary there are many factors affecting the frictional resistance, and the comprehensive effects of various factors must be considered in the perspective of mechanics and tribology.

The seal membrane is preferably produced from rubber such as natural rubber, silicone or polyisoprene, its mechanical properties including super elastic and viscoelastic. Although the mechanical model of the rubber deformation process is complicated, it can still apply the generalized Hooke's law to describe approximatively its elastic behavior; and Newton's internal friction law to describe the viscous behavior. Research suggests that the main factors affecting the friction of the two surfaces in contact between the rubber and the instrument include: the smaller the friction coefficient of said two surfaces, the smaller the friction is; the better lubrication condition of said two surfaces in contact, the friction smaller is; the smaller normal pressure of said two surfaces, the friction smaller is. Comprehensively considering the above factors, the present invention proposes better solutions for reducing the frictional resistance between the seal membrane and the inserted instrument.

In addition to said frictional resistance greatly affecting the performance of the cannula assembly, the stick-slip of the seal membrane is another main factor affecting the performance of trocar. Said stick-slip means that when the instrument moves longitudinally in the sleeve, the sealing lip and lip-adjacent area sometimes are relatively statically attached to the instrument (at this point, the friction between the instrument and the seal membrane is mainly static friction); but sometimes it produced a relatively slippery phenomenon with the instrument (at this point, the friction between the instrument and the seal membrane is mainly dynamic friction); and said static friction is much greater than said dynamic friction. The two frictions alternately occur, which causes the movement resistance and speed of the instrument in the seal membrane to be unstable. It is easy to be understood for those skilled in the art, that in minimally invasive surgery the surgeon can only use surgical instruments to touch (feel) the patient's organs and observe a part of the working head of the instruments through endoscopic image system. In this case where the vision is limited and it cannot be touched, the surgeon typically uses the feedback of the resistance when moving, instruments as one of the information to judge whether the operation is abnormal nor not. The stick-slip affects the comfort of operation, the accuracy of positioning, and even induces the surgeon to make false judgment.

During the surgical application of the cannula, the stick-slip is difficult to avoid, but can be reduced. Researches have shown that said stick-slip is affected by two main factors: one is that the smaller the difference between the maximum static friction and the dynamic friction, the weaker the stick-slip is; the other is that the larger the axial tensile stiffness of the seal membrane, the weaker the stick-slip is. Avoiding excessive the hoop force between the seal membrane and the instrument, reducing the two surfaces contacted, maintaining good lubrication, respectively, can reduce the difference between the maximum static friction and the dynamic friction, thereby reducing stick-slip, meanwhile, increasing the axial tensile stiffness of the seal membrane also helps to reduce the stick-slip phenomenon. The invention also proposes measures for improving stick-slip.

In summary, so far, there is no cannula that can effectively solve the said problems.

SUMMARY OF PRESENT INVENTION

In conclusion, one object of the invention is to provide a trocar seal membrane, said seal membrane comprises a proximal opening, a distal aperture, and a sealing wall from the distal aperture extending to the proximal opening, said distal aperture formed by a sealing lip for accommodating the inserted instrument and forming a gas-tight seal. Said the sealing wall includes a proximal surface and a distal surface. Said seal membrane can ensure a reliable seal for the inserted 5 mm instrument, and reduce frictional resistance and improve stick-slip when a large-diameter instrument is inserted.

As described in the background, the wrapped area formed by the sealing lip and the lip-adjacent area when a large diameter instrument inserted, is the major factor cause of frictional resistance. For reducing said frictional resistance, comprehensive consideration should be given such as reducing the radial stress between the instrument and the seal membrane, reducing said wrapped area, and reducing the actual contact area of the two surfaces. It is easy to understand for those skilled in the art that in accordance with the generalized Hooke's law and Poisson effect, enlarge hoop circumference, and reduce hoop strain (stress), thereby reducing radial strain (stress). But it should be noted that it is impossible to enlarging the hoop circumference in order to reduce the strain of the sealing lip which will result in reduced sealing reliability when applying 5 mm instruments. Since the stress in the lip-adjacent area is highly concentrated when applying a large diameter instrument, the hoop circumference of the lip-adjacent area should be rapidly increased. In regard to outside the lip-adjacent area, since the strain (stress) is small, it is not necessary to adopt measures to enlarge the hoop circumference. In addition, enlarging the hoop circumference, in the meantime increasing the axial tensile stiffness in the lip-adjacent area and maintain good lubrication (reducing difference between the maximum static friction and dynamic friction), thereby the stick-slip in the lip-adjacent area is improved.

In one aspect of the invention, said seal membrane comprises a proximal opening, a distal aperture, and a sealing wall from the distal aperture extending to the proximal opening, said sealing wall comprising a proximal surface and a distal surface. Said distal aperture formed by a sealing lip for accommodating the inserted instrument forms a gas-tight seal, and said sealing lip is cylindrical. Said sealing wall is a seamless sealing body with a plurality of normal concave-channels and a plurality of reverse concave-channels surrounding the sealing lip in an alternating manner. Said normal concave-channels are recessed from the proximal surface of the sealing wall toward the distal surface and the opening oriented to the proximal surface; Said reverse concave-channels are recessed from the distal surface of the sealing wall toward the proximal surface and the opening oriented to the distal surface. Said normal concave-channels and said reverse concave-channels extend laterally outward from the sealing lip, and the depth of said normal concave-channels and said reverse concave-channels gradually increases in the lip-adjacent area; Said seal membrane also includes a flange and a cliff which extends from the flange to distal end, and simultaneously intersects said normal concave-channels and reverse concave-channels. Optionally, said seal membrane also includes an outer floating portion with at least one lateral pleat extending from the flange to the proximal opening. Said normal concave-channels and reverse concave-channels are distributed in frustum shape, and the numbers of them both are 8. In an alternative embodiment, the thickness of normal concave-channel and reverse concave-channel is substantially uniform. In another alternative embodiment, the internal width of said channels in the lip-adjacent area is B, wherein 0.5 mm≤B≤1 mm.

In another aspect of the present invention, a seal membrane assembly includes said seal membrane, a lower retainer ring, an upper retainer ring, and a protection device. Said lower retainer ring includes a proximal surface, a distal surface, a support-wall extending from the distal surface to the proximal surface, and a plurality of hooked cantilevers which connected to the support-wall and extending from the distal surface the proximal surface. Said seal membrane and said protect device are sandwiched between the upper retainer ring and the lower retainer ring. Moreover, said hooked cantilever are inserted into the reverse concave-channels of said seal membrane and are closed to the cliff of said seal membrane. However, a sufficient gap is reserved between said support-wall of the lower retainer ring and said annual wall to realize the function of allowing diastolic deformation of the cliff and limit the inversion deformation of the seal membrane.

The structure of normal and reverse concave-channels alternately distributed in circular array has the functions of enlarging hoop circumference, reducing the wrapped area, reducing the actual contact area of the two surfaces between the instrument and the seal membrane, improving lubrication reliability, increasing the axial tensile stiffness, etc., thereby, the frictional resistance and the stick-slip can be greatly reduced, and the probability of inversion is reduced and the comfort of application is improved.

In another aspect of the invention, said seal membrane comprises a proximal opening, a distal aperture, and a sealing wall from the distal aperture extending to the proximal opening, said sealing wall comprising a proximal surface and a distal surface. Said distal aperture formed by a sealing lip for accommodating the inserted instrument forms a gas-tight seal, and said sealing lip is circular. Said sealing wall is a seamless sealing body with a plurality of normal concave-channels and a plurality of reverse concave-channels surrounding the sealing lip in an alternating manner. Said normal concave-channels are recessed from the proximal surface of the sealing wall toward the distal surface and the opening oriented to the proximal surface; said reverse concave-channels are recessed from the distal surface of the sealing wall toward the proximal surface and the opening oriented to the distal surface. Said normal concave-channels and said reverse concave-channels extend laterally outward from the sealing lip, and the depth of said normal concave-channels and said reverse concave-channels gradually increases in the lip-adjacent area; said seal membrane also includes a flange and a cliff which extends from the flange to distal end, and simultaneously intersects said normal concave-channels and reverse concave-channels. Said normal concave-channels and reverse concave-channels are distributed in a hemispherical manner around the sealing lip.

In another aspect of the invention, said seal membrane comprises a proximal opening, a distal aperture, and a sealing wall from the distal aperture extending to the proximal opening, said sealing wall comprising a proximal surface and a distal surface. Said distal aperture formed by a sealing lip for accommodating the inserted instrument forms a gas-tight seal; said sealing lip is cylindrical. In the lip-adjacent area, said sealing wall is a seamless sealing body with a plurality of normal concave-channels and a plurality of reverse concave-channels surrounding the sealing lip in an alternating manner. Said normal concave-channels are recessed from the proximal surface of the sealing wall toward the distal surface and the opening oriented to the proximal surface; Said reverse concave-channels are recessed from the distal surface of the sealing wall toward the proximal surface and the opening oriented to the distal surface. Said normal concave-channels and said reverse concave-channels extend laterally outward from the sealing lip, and the depth of said normal concave-channels and said reverse concave-channels gradually increases in the lip-adjacent area; said seal membrane also includes a flange and a cliff which extends from the flange to distal end, and simultaneously intersects said normal concave-channels and reverse concave-channels. In one embodiment, the bottom surface of said reverse concave-channels is a plane in the lip-adjacent area, while which is a curved surface recessed from the distal surface toward the proximal surface, which surface has better effect of for preventing the seal inversion.

Another object of the invention is to provide a trocar seal assembly, which including a lower retainer ring, a seal membrane, a rigid upper retainer ring, a protection device, an upper body and an upper cover. Said the seal membrane and said protection device are sandwiched between the lower retainer ring and the upper retainer ring, said protection device permit the sharp edge of the instrument to pass through without causing perforations or tears to the seal membrane; said seal membrane also includes a flange at which said normal concave-channels and reverse concave-channels extends to be intersected, and an outer floating portion including at least one lateral pleat extending from the flange to the proximal opening, which is sandwiched between said upper body and said upper cover, and said outer floating portion makes said seal membrane and protector float laterally in the housing formed by the upper body and the cover.

It is believed that the above invention or other objects, features and advantages, will be understood with the drawings and detailed description.

DESCRIPTION OF THE DRAWINGS

A more complete appreciation of this invention, and many of the attendant advantages thereof will be readily apparent as the same becomes better understood by reference to the following detailed description, where.

In all views, the same referred number shows the same element or assembly.

DETAILED DESCRIPTION OF PREFERRED EMBODIMENTS

Embodiments of the invention are disclosed herein, however, it should be understood that the disclosed embodiments are merely examples of the invention, which may be implemented in different ways. Therefore, the invention is not intended to be limited to the detail shown, rather, it is only considered as the basis of the claims and the basis for teaching those skilled in the art how to use the invention.

Figures 1, 2:
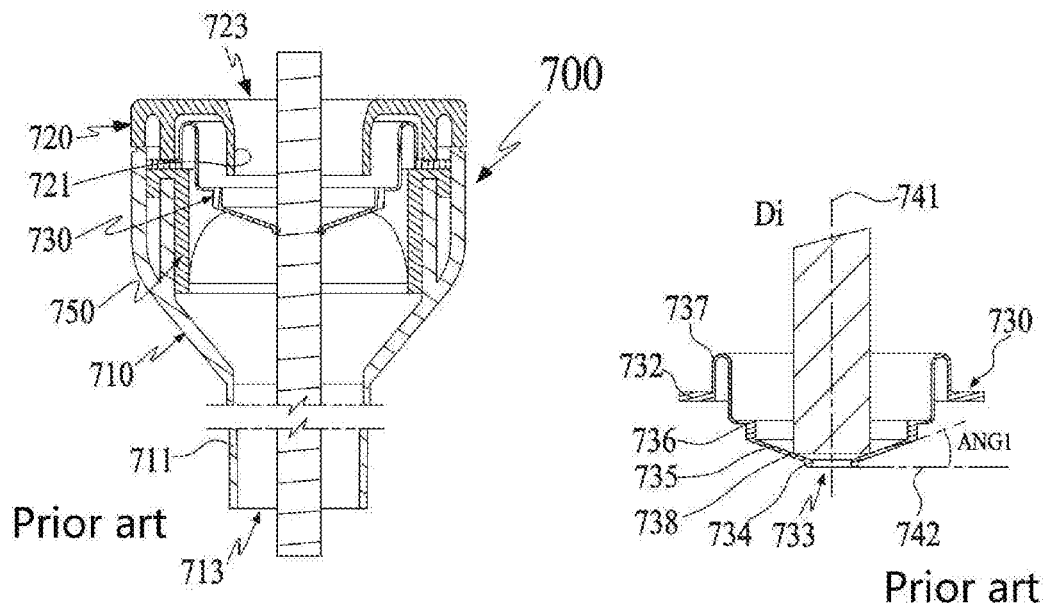
FIG. 1: shows a simulated distorted view of the cannula with the 5 mm diameter instrument inserted in the prior art.
FIG. 2: shows a detailed view of the seal membrane 730 in the prior art.
Figures 3, 4:
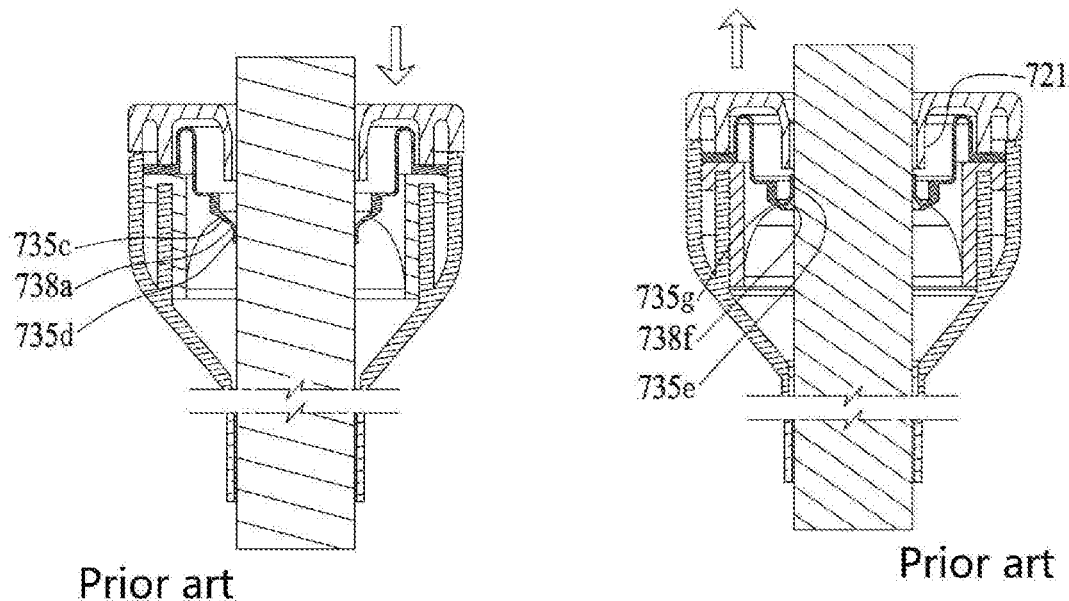
FIG. 3: shows a simulated distorted view of the cannula with the 12.8 mm diameter instrument inserted in the prior art.
FIG. 4: shows a simulated distorted view of the cannula with the 12.8 mm diameter instrument removed in the prior art.
Figure 5:
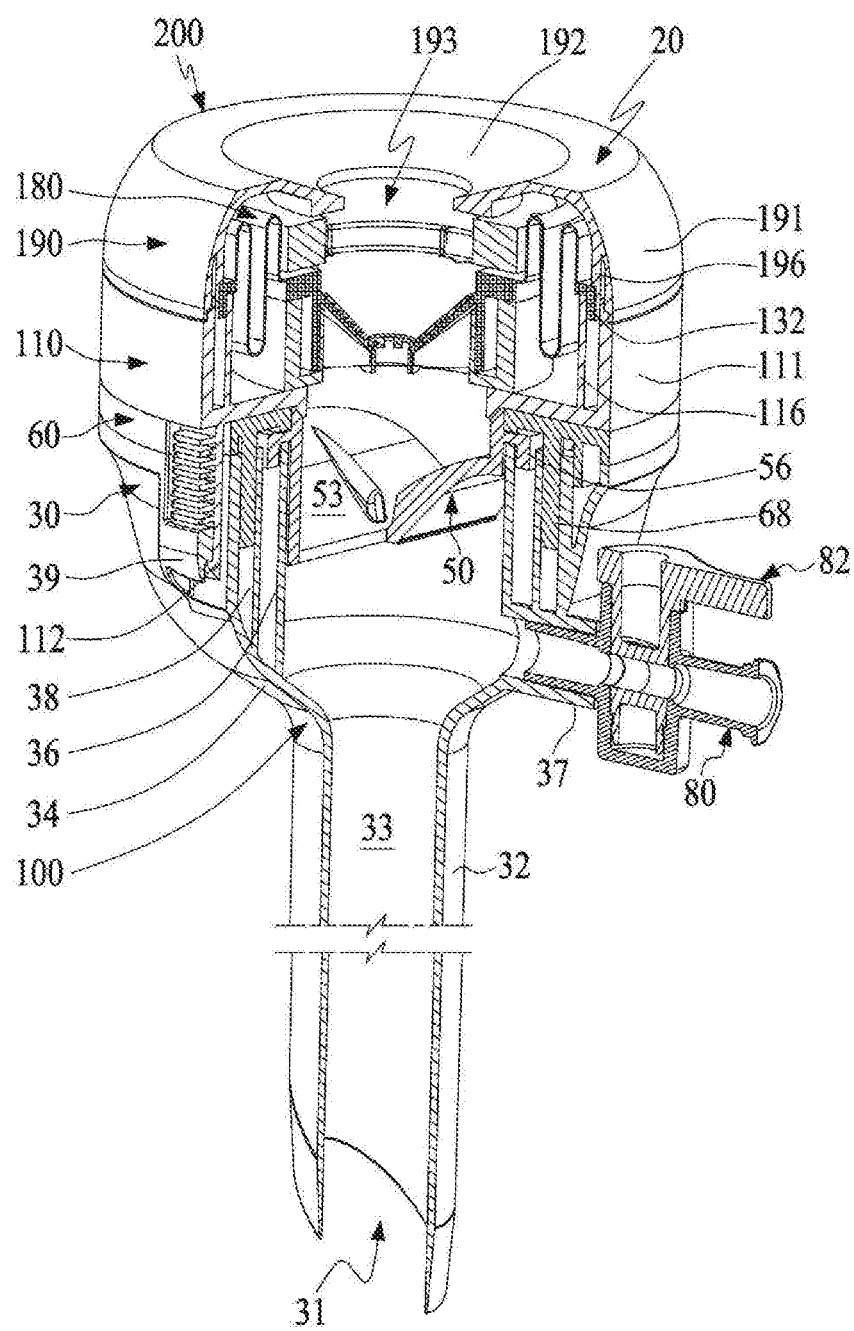
FIG. 5: shows a 3D perspective partial sectional view of the cannula in the invention.

FIG. 5 shows an overall view of the structure of trocar. A typical trocar comprises an obturator 10 (not shown) and a cannula 20. The cannula 20 comprises an open proximal end 192 and an open distal end 31. In a typical embodiment, said obturator 10 passes through said cannula 20, together they facilitated penetration of the abdominal wall through incision into the body cavity. Once penetrated into the body cavity, the obturator 10 is removed, and the cannula 20 will be left as access for the instrument get in/out of the body cavity. Said proximal end 192 in the external position of the patient and said distal end 31 in the internal position. A preferred cannula 20 can be divided into the first seal assembly 100 and the second seal assembly 200. Locking receptacle 39 in said seal assembly 100 can be locked with snap-in projection 112 in said seal assembly 200. The cooperation of snap-in projection 112 and the locking receptacle 39 can be quick release by one hand. The main purpose is for convenience of taking out tissues or foreign matter from the patient in the surgery. There are multiple ways to implement the quick release connection of said seal assembly 100 and assembly 200. In addition to the structure shown in this embodiment, a threaded connection, a rotary snap-in or other quick lock structure also may be applied. Alternatively, said assembly 100 and assembly 200 can be designed as a structure that can not be split quickly.

FIG. 5 shows the composition and assembly relationship of the first seal assembly 100. The lower body 30 includes an elongated tube 32, which defines the sleeve 33 passed through the distal end 31 and is connected to the outer housing 34. Said lower body 30 comprises an inner wall 36 supporting duck bill seal and a valve bore 37 that communicates with the inner wall 36. The plunger 82 mounted in the valve body 80, the said two are mounted into said valve bore 37. The flange 56 of the duck bill seal 50 is sandwiched between the inner wall 36 and the lower cover 60. There are various ways of fixing between the lower cover 60 and the lower body 30, such as the interference fit, ultrasonic welding, glue bonding, and snap fastening. 4 cylinders 68 of said lower cover 60, in this embodiment, 4 holes 38 of said lower body 30 are adopted to interference fit, so that the duckbill seal 50 is in the compressed state. Said tube 32, said the inner wall 36, said duck bill seal 50, said valve body 80 and said plunger 82 together are comprised the first chamber. Said duck bill seal 50, in this embodiment, is a single-slit, while other types of closure valves may also be used, including flapper valves, multi-silted cluck bill valves. When the instrument is passed through said duck bill seal 50, the duckbill 53 will be opened, but it generally does not provide a complete seal against the instrument. When the instrument is removed, said duckbill 53 closed and substantially prevents insufflation fluid from escaping through the first chamber.

FIG. 5 shows the composition and assembly relationship of the second seal assembly 200. The seal membrane assembly 180 is sandwiched between the upper cover 110 and the upper body 190. The proximal end 132 of the seal membrane assembly 180 is secured between the inner ring 116 of the upper cover 110 and the inner ring 196 of the upper body 190. There are various secured ways between the upper body 190 and the upper body 110, such as the interference fit, ultrasonic welding, glue bonding, and snap fastening. The connection method, shown in this embodiment, is the outer shell 191 of the upper body 190 and the outer shell 111 of the upper cover 110 are secured by ultrasonic welding, so that the proximal end 132 of the seal membrane assembly 180 is in the compressed state. The center hole 113 of said upper cover 110, said inner ring 116, and said seal membrane assembly 180 together are comprised the second chamber.

Figure 6:
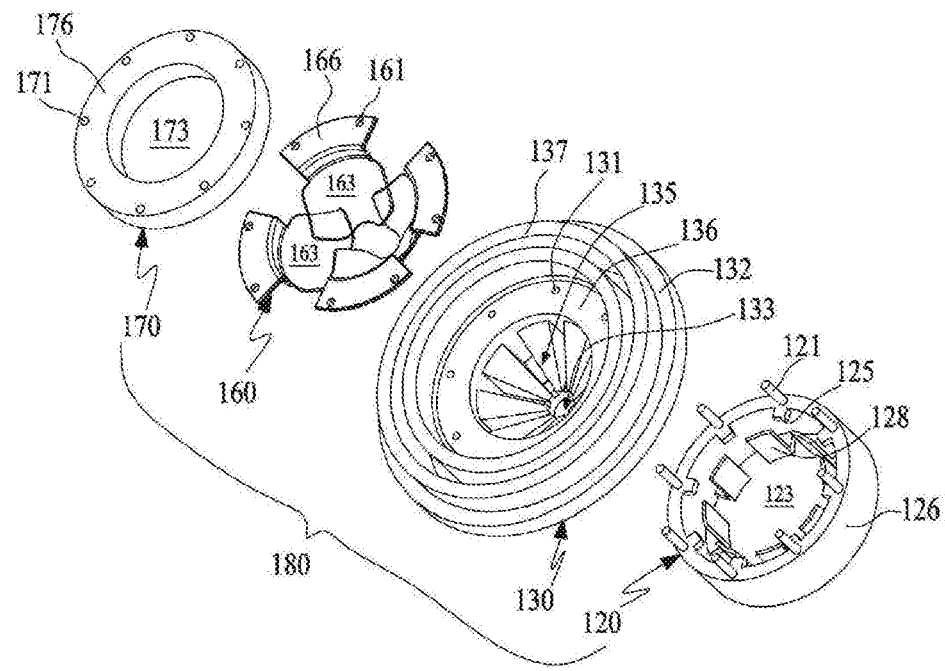
FIG. 6: shows an exploded view of the seal membrane assembly of the cannula in FIG. 5.
Figure 7:
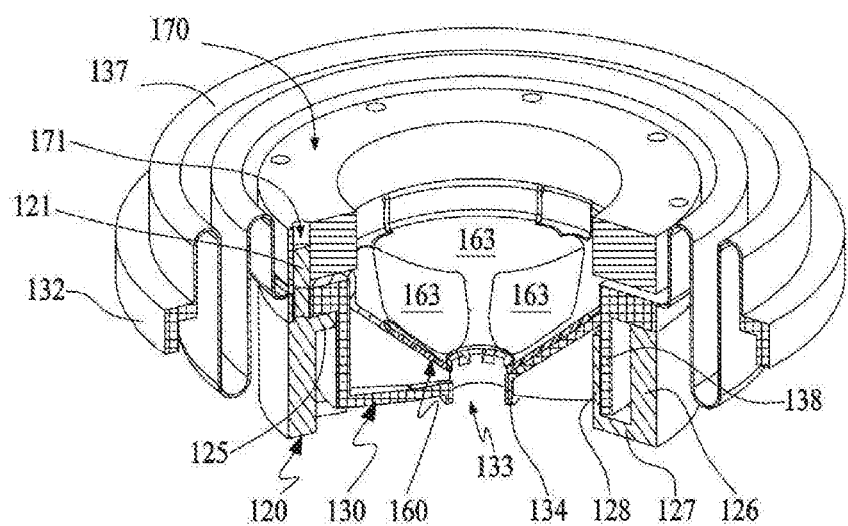
FIG. 7: shows a 3D perspective partial sectional view of the seal membrane assembly in FIG. 6.
Figure 8:
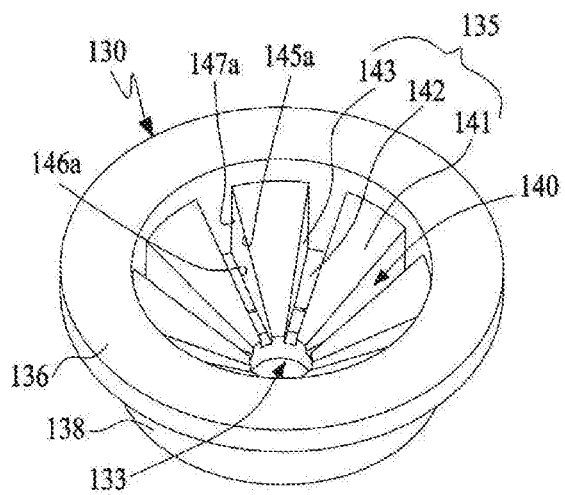
FIG. 8: shows a 3D perspective view of the seal membrane without the proximal end and floating portion in FIG. 6.
Figure 9:
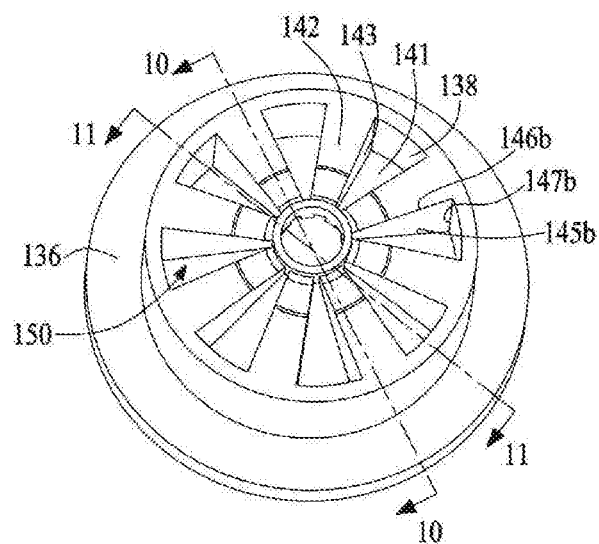
FIG. 9: shows a 3D perspective reverse view of the seal membrane in FIG. 8.
Figure 10:
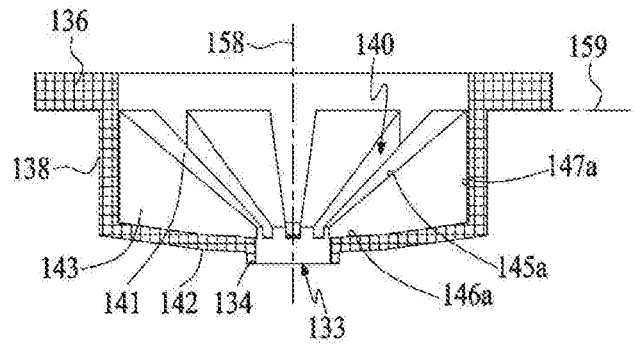
FIG. 10: shows a sectional view along line 10-10 in FIG. 9.
Figure 11:
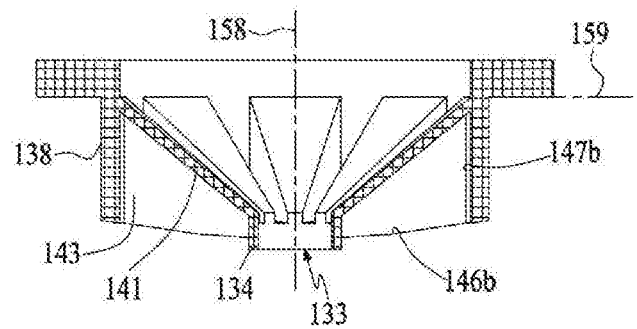
FIG. 11: shows a sectional view along line 11-11 in FIG. 9.

FIG. 6-7 illustrate the composition and assembly relationship of said seal membrane assembly 180, which including a lower retainer ring 120, a seal membrane 130, a protection device 160 and an upper retainer ring 170. Said the seal membrane 130 and said protection device 170 are sandwiched between the lower retainer ring 120 and the upper retainer ring 125, moreover, the cylinder 121 of the said lower retainer ring 120 is aligned with corresponding holes on other components in said seal membrane assembly 180. Said cylinder 121 and the bore 171 of the upper retainer ring 170 are adopted to interference fit, so that the whole seal membrane assembly 180 is in the compressed state. Said protection device 160 includes 4 protectors 163 arranged so as to protect a center sealing body of said seal membrane 130, herein permit the sharp edge of the instrument to pass through without causing perforations or tears to the seal membrane 130.

Said seal membrane 130 includes a proximal opening 132, a distal end aperture 133, and the sealing wall extending from the distal end to the proximal end, said sealing wall including a proximal surface and a distal surface. Said aperture 133 formed by a sealing lip 134 for accommodating an inserted instrument and forming a gas-tight seal. Said sealing lip 134, in the present embodiment, is approximately cylindrical, but said sealing lip 134 may be not circular.

Said the seal membrane 130 also including the flange 136; The sealing wall 135 has one end connected to the sealing lip 134 and the other end connected to the flange 136; the floating portion 137 has one end connected to the flange 136 and the other end connected to said proximal end 132. Said flange 136 for mounting the protector device 160. Said floating portion 137 including one or several plurality of radial (lateral) pleats, so that the entire seal membrane assembly 180 can float in the assembly 200.

Said assembly 180 can be made from a variety of materials with a range of different properties. For instance, said seal membrane 130 is made of a super elastic material such as silicone or polyisoprene; said protector device 160 is made of a semi-rigid thermoplastic elastomer; and said second retainer ring 120 and said first retainer ring 170 are made of a relatively hard rigid material such as polycarbonate.

FIG. 8-11 show more detailed depiction the seal membrane 130 of the first embodiment of the invention. In order to reduce the production cost, the seal membrane 130 is preferably designed as a monolithic part, but can also be designed as an inner seal body and an outer floating portion, separated from the flange 136. The first embodiment is mainly directed to the improvement of the inner seal body. To simplify the description, the outer floating portion and the proximal end are not shown in the subsequent description of the seal membrane. Defining a transverse plane 159 that is generally perpendicular to the longitudinal axis 158.

Defining the axis of said sealing lip 134 as the longitudinal axis 158, and a transverse plane 159 that is generally perpendicular to the longitudinal axis 158. Said sealing wall 135, the shape of which can be approximately frustum, approximately hemispherical, or an irregularly rotating surface. In this embodiment, said wall 135 is formed in an approximately conical arrangement surrounding the sealing lip 134. Said wall 135 including an inner sealing-wall 141, an outer sealing-wall 142 and a side sealing-wall 143. Said inner sealing-wall 141 extends laterally from the sealing lip 134 to the cliff 138; said an outer sealing-wall 142 extends laterally from the sealing lip 134 to said cliff 138; while said cliff 138 and the flange 136 are intersected. The first side of said side sealing-wall 143 intersects the inner sealing-wall 141 and forms a line 145a, 145b; the second side of said side sealing-wall 143 intersects the outer sealing-wall 142 to form a line 146a, 146b; the third side of said side sealing-wall 143 intersects said cliff 138 to form an intersection line 147a, 147b.

Defining the angle between said intersection line 145a (145b) and the transverse plane surface 159 as α, which is called the guide angle α, defining the angle between said intersection line 146a (146b) and said transverse plane surface 159 as β, which is called the guide angle, and $0 \leq \beta < \alpha < 90°$. When β=0°, the rotary wall is parallel to the transverse plane 159. The angle between said intersection line 145b and said intersection line 146b (or 145a and 146a) is defined as θ. The intersection of the two intersection lines (i.e. the apex of the angle θ) may be on the sealing lip 134; or the virtual extension lines of the two intersection lines intersect the inside of the sealing lip 134. In the lip-adjacent area, the side sealing-wall 143 is a surface defined by both sides and extending laterally outward from the sealing lip 134 and gradually widening.

FIG. 8-11 show said 2 adjacent side sealing-wall 143 and the outer sealing-wall 142 there between form a channel that is recessed from the proximal surface toward the distal surface and the opening oriented to the proximal surface, which is defined as the normal concave-channel 140; meanwhile, said 2 adjacent side sealing-wall 143 and the inner sealing-wall 141 there between form a channel that is recessed from the distal surface toward the proximal surface and the opening oriented to the distal surface, which is defined as the reverse concave-channel 150. Said inner sealing-wall 141, said side sealing-wall 143 and said outer sealing-wall 142 forms a series of normal concave-channel and reverse concave-channel, and said normal concave-channel and reverse concave-channel alternately distributed in circular array around the sealing lip 134, extending laterally outward and gradually increasing in axial depth. The adjacent normal concave-channel and the reverse concave-channel sharing a mutual side sealing-wall, and a series of normal and reverse concave-channels alternately distributed with increasing axial depth form a seamless sealing wall 135.

Said cliff 138 extends from the flange 136 toward the distal end and simultaneously intersects normal concave-channels 140 and the reverse concave-channels 150. The cliff 138 is a complete rotary cliff, said cliff 138 and the reverse concave-channels 150 intersect to form a complete grooves. Said cliff 138 helps to prevent the seal inversion; and when inversion occurs, if the instrument is removed, said 138 allows the seal membrane to spring back, thereby facilitating reinsertion of the instrument. In the present embodiment, the shape of said cliff 138 is approximately cylindrical, while it can be an approximately frustum or irregular rotary wall.

Figure 12:
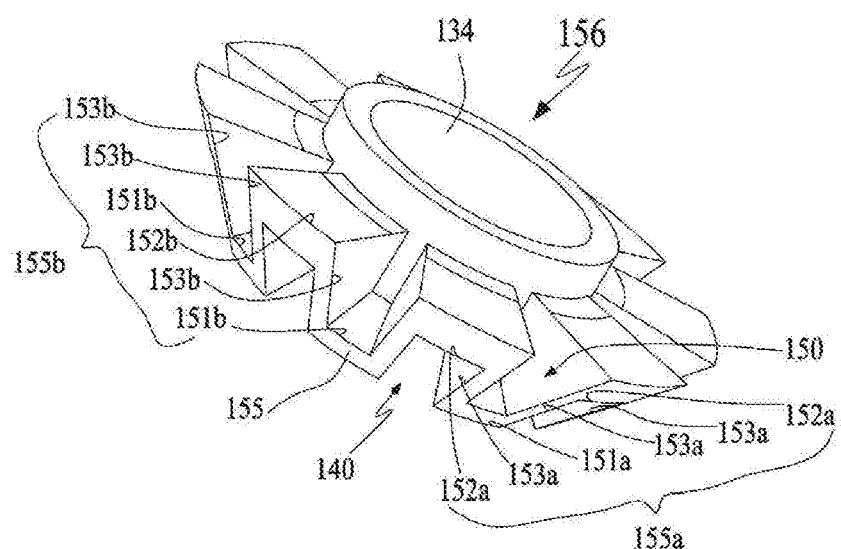
FIG. 12-13: shows a segmentation view of the seal membrane after the circumferential cutting separation in FIG. 9.
Figure 13:
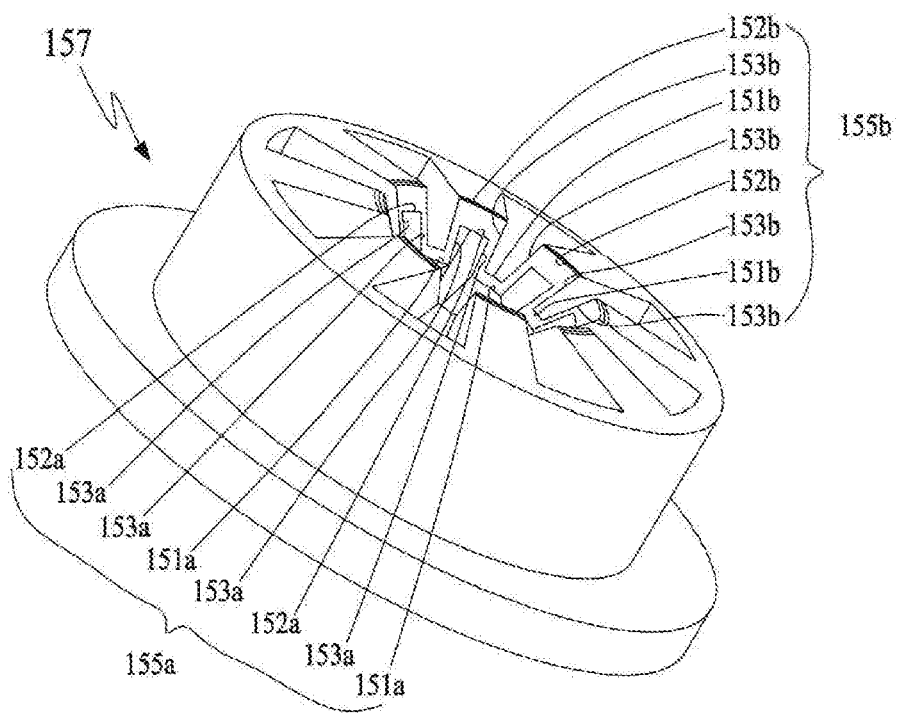

FIG. 12-13 illustrates, in an alternative embodiment, the thickness of normal concave-channel and reverse concave-channel is substantially uniform. That is, the thickness of the inner sealing-wall 141, the outer sealing-wall 142 and the side sealing-wall 143 is substantially equal. Said substantially uniform thickness causes the deformation of the sealing wall 135 to be substantially uniform. However, said substantially uniform thickness should not be limited to the absolute equality of the values. When the number of said channels is numerous, the thickness of the side sealing-wall 143 can be 0.05~0.25 mm thinner than the thickness of the inner sealing-wall 141 (or the outer sealing-wall 142) for convenience of measurement. The thickness value of the inner sealing-wall 141, the outer sealing-wall 142 and the side sealing-wall 143 is small, for convenience of quantification, the thickness ratio between the inner sealing-wall 141 (or the outer sealing-wall 142) and said side sealing-wall 143 within 1~1.5, which still approximately consider that the thickness of the sealing wall 135 is substantially uniform and still does not deviate from the scope of the invention.

The sealing wall 135, in the present embodiment, comprises 8 linear normal concave-channels and 8 reverse concave-channels, however, a greater number or a smaller number of non-linear reverse concave-channel may be adopted. The side sealing-wall 143 of the present embodiment is substantially parallel to the longitudinal axis 158, and in the lip-adjacent area, make a arbitrarily section plane that parallel to said axis 158 and meanwhile perpendicular to any one of said side sealing-walls 143, the intersected profile formed by said section plane and said channels 140 and reverse concave-channels 150 is approximately U-shaped (the intersected profiles of other channels are also defined in this way). For convenience of manufacture, such as mold unloading, said side sealing-walls 143 may not be parallel to the longitudinal axis 158; that is, the section of said normal concave-channel 140 or the reverse concave-channel 150 is approximately trapezoidal, even approximately V-shaped.

Taking the longitudinal axis 158 as a rotary axis, make a cylindrical surface with a radius R1 and intersects with the inner sealing-wall 141 to form an intersection line, and create cutting plane M1 through said intersection line and perpendicular to the generating line of said inner sealing-wall 141 (with the axis 158 as rotary axis). Said cutting plane M1 divides the seal membrane 130 into an inner portion 156 (as in FIG. 12) and, an outer portion 157 (FIG. 13). Said cutting plane M1 intersects said inner sealing-wall 141 to form a plurality of intersection lines 151a and 151b. Said cutting plane M1 intersects the side sealing-wall 143 to form a plurality of intersection lines 153a and 153b, and said cutting plane M1 intersects the outer sealing-wall 142 to form a plurality of intersection lines 152a and 152b. The plurality of segments 151a, 152a, 153a are formed an annular intersection line 155a; the plurality of segments 151b, 152b, 153b are formed an annular intersection line 155b, and the section 155 defined by said annular intersection line 155a and 155b.

As shown in FIG. 12-13, it is obvious that the circumference L1 of the intersection line 155a (155b) is much larger than $2*\pi*R1$, that means the reverse concave-channel plays a role in enlarging hoop circumference, and the difference between L1 and $2*\pi*R1$ is approximately equal to $2*P$ times the length L2 of the intersection line 153a (153b) (P is the number of reverse concave-channels). That is, the side sealing-wall 143 actually plays a role in enlarging hoop circumference. With the prerequisite of the reverse concave-channels width meeting the needs of the manufacturer, increasing the width of the reverse concave-channel does not mean have a larger hoop circumference.

Those skilled in the art can understand that there must be some R1 value making the outer portion 157, which is divided by the cutting plane M1, to start from the section 155, the main change of its shape is shown as local bending deformation and macroscopic displacement of the seal membrane, rather than the overall microscopic molecular chain elongation and overall tensile deformation. And said inner portion 156, from said sealing lip 134 to said section 155, the change of shape is shown as the comprehensive effect of partial bending deformation and overall tensile deformation of the seal membrane. What it is quite clear is that said reverse concave-channels enlarge hoop circumference, and reduce the cylinder hoop strain (stress) when a large diameter instrument is inserted, thereby reducing the hoop force and the frictional resistance.

Figure 14:
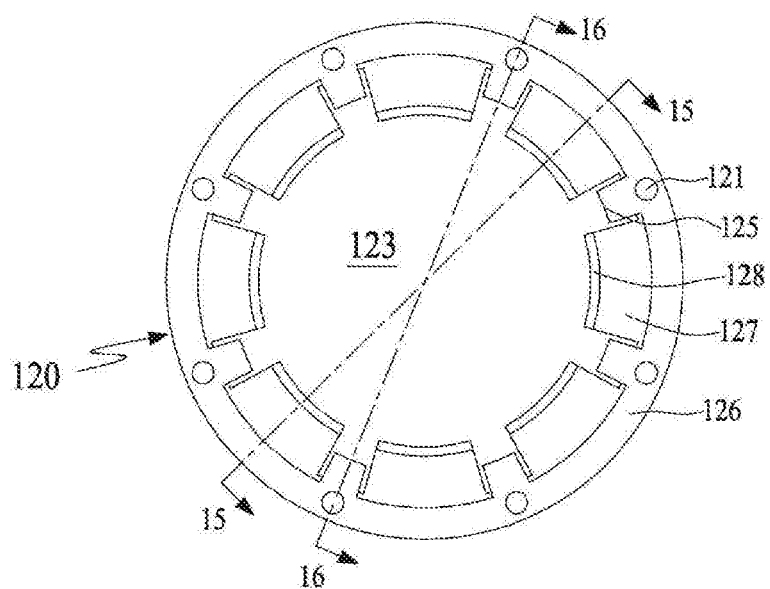
FIG. 14: shows a flattened projection view of the lower retaining ring in FIG. 6.
Figure 15:
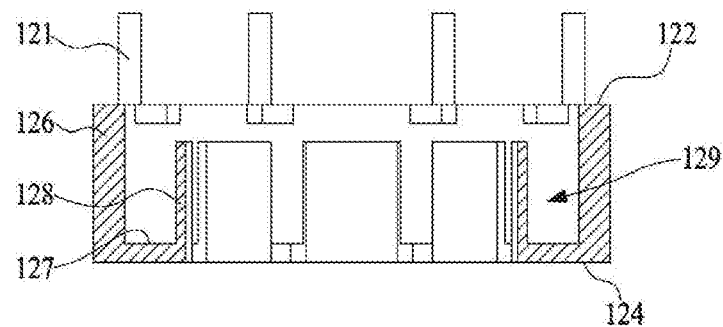
FIG. 15: shows a sectional view along line 15-15 of the lower retaining ring in FIG. 14.
Figure 16:
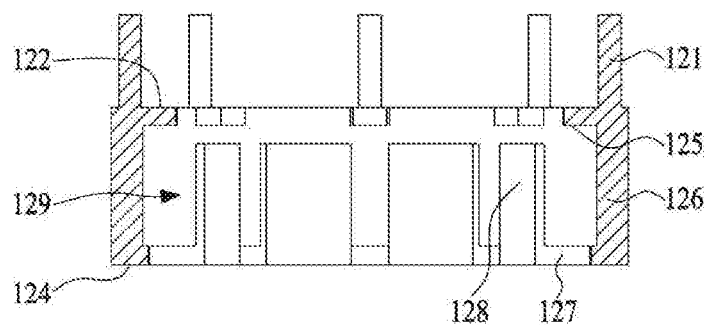
FIG. 16: shows a sectional view along line 16-16 of the lower retaining ring in FIG. 14.

FIG. 14-16 depict the structure of the lower retainer ring 350 in more detail. Said lower retainer ring 120 comprises a proximal surface 122, a distal surface 124, and an annular-shell 126 extending from the distal end to the proximal end; said annular-shell 126 defines through-holes 123. A plurality of retainer posts 121 extend outward from the proximal surface 122, a plurality of steps 125 extend from the proximal surface 122 toward the center of the annular-shell 126. A plurality of arms 127 extend from the distal surface 124 toward the center of the annular-shell 126, the arm 128 intersects the arm 127 and extends from the distal end toward the proximal end, and the arm 127 and the arm 128 constitute an L-shaped hooked cantilever 129. And referring to FIG. 7, in the assembly 180, the hooked cantilever 129 matches the reverse concave-channels 150; that is, said arm 128 is inserted into the reverse concave-channels 150, and the arm 128 is adjacent to the cliff 138 away from the annular-shell 126.

Figure 17:
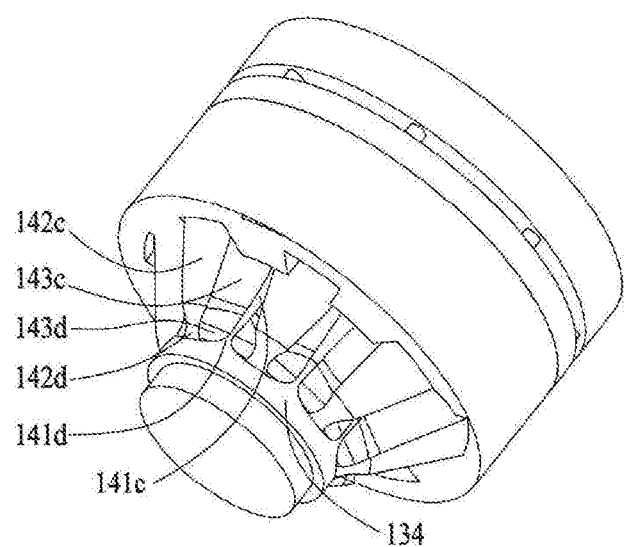
FIG. 17: shows a simulated distorted view of the cannula with the 12.8 mm diameter instrument inserted in FIG. 7.
Figure 18:
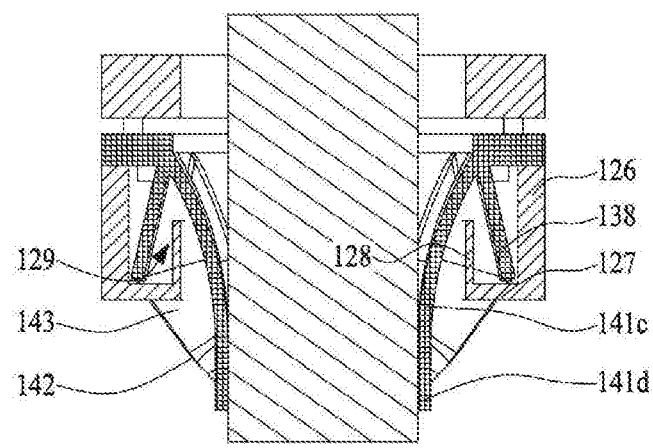
FIG. 18: shows a simulated distorted longitudinal view illustrated in FIG. 17.

FIG. 17-18 shows a simulated deformation view of the seal membrane 130 when a large diameter instrument is inserted into said seal membrane assembly 180 (the floating portion outside the seal membrane and the protect device 160 are not shown). Said inner sealing-wall 141 is divided into two portions, an inner sealing-wall 141c and a cylindrical-wall 141d; said outer sealing-wall 142 is divided into two portions, an outer sealing-wall 142c and a cylindrical-wall 142d; said side sealing-wall 143 is divided into two portions, a side sealing-wall 143c and a cylindrical-wall 143d. Said cylindrical-wall 141d, said cylindrical-wall 142d, and said cylindrical-wall 143d together forms the wrapped-area around the outer surface of said inserted instrument. Studies have shown that, compared to the grooveless design, the wrapped-area of the seal membrane with the channel is small, and reducing the wrapped-area can reduce the frictional resistance.

In the present embodiment, the structure of said normal and reverse concave-channels enlarge hoop circumference, and said side sealing-wall 143 increases local bending stiffness of the sealing wall 135. Referring to FIG. 18 Said sealing lip 134 is stretched enough to accommodate the inserted instrument, the sealing wall 135 rotates and stretches outwardly around its intersection part with the flange 136; and said side sealing-wall 143 forces the cliff 138 to rotate and stretch outwardly around its intersection part with the flange 136 too. In the present embodiment, a sufficient gap is reserved between the cliff 138 and said annular-shell 126, so said sealing wall 135 and the cliff 138 are free to be stretched and deformed outwardly, and there is no (or very small) extrusion force between said cliff 138 and the annular-shell 126, thereby reducing the normal pressure of said two surfaces in contact between the wrapped-area and the instrument.

Figure 19:
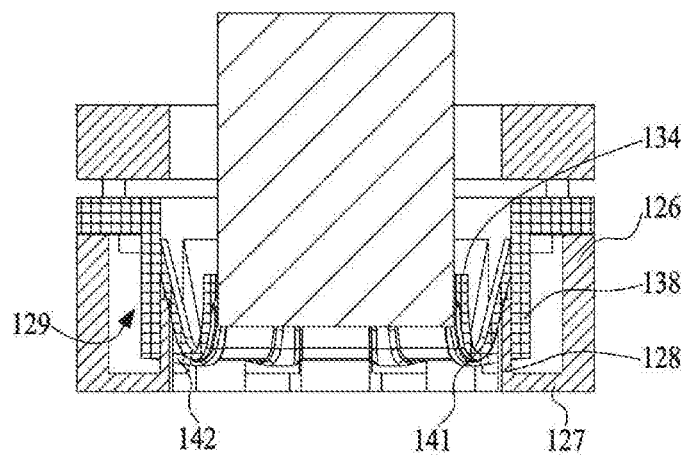
FIG. 19: shows a simulated distorted view of the cannula with the 12.8 mm diameter instrument inserted in FIG. 18.
Figure 20:
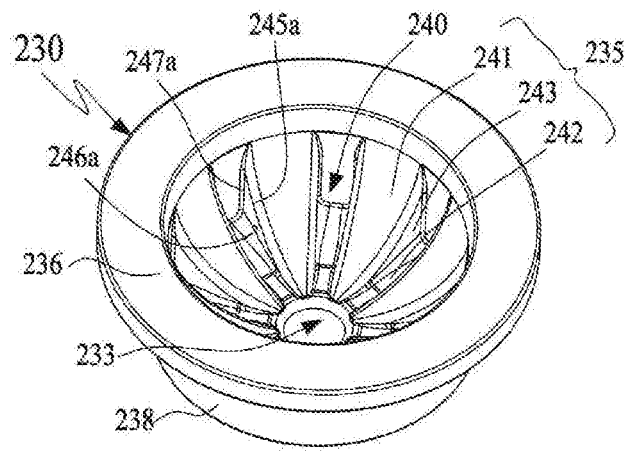
FIG. 20: shows a 3D perspective view of the seal membrane of another embodiment according to the invention.
Figure 21:
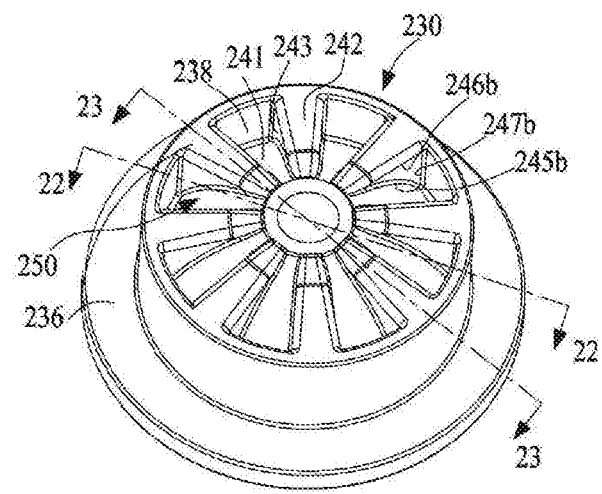
FIG. 21: shows a 3D perspective reverse view of the seal membrane in FIG. 20.
Figure 22:
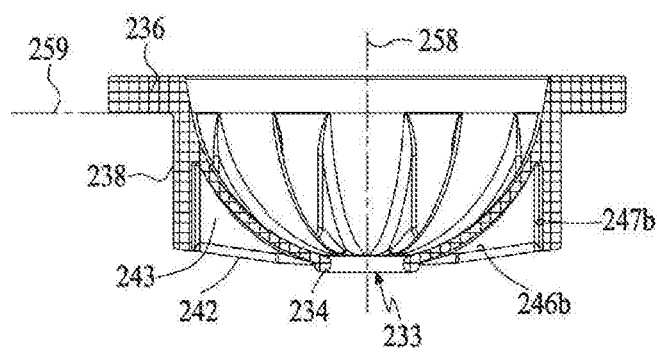
FIG. 22: shows a partial view along-line 22-22 in FIG. 21.
Figure 23:
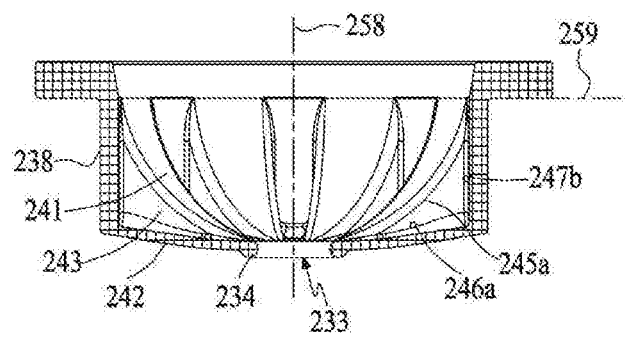
FIG. 23: shows a partial view along-line 23-23 in FIG. 21.
Figure 24:
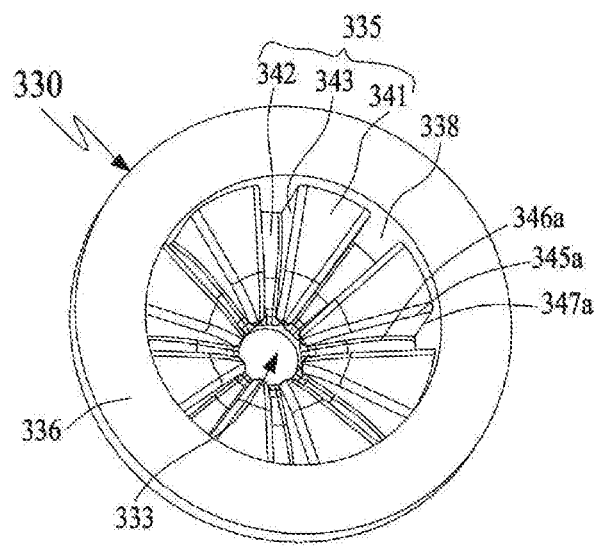
FIG. 24: shows a perspective view of the seal membrane of another embodiment according to the invention.
Figure 25:
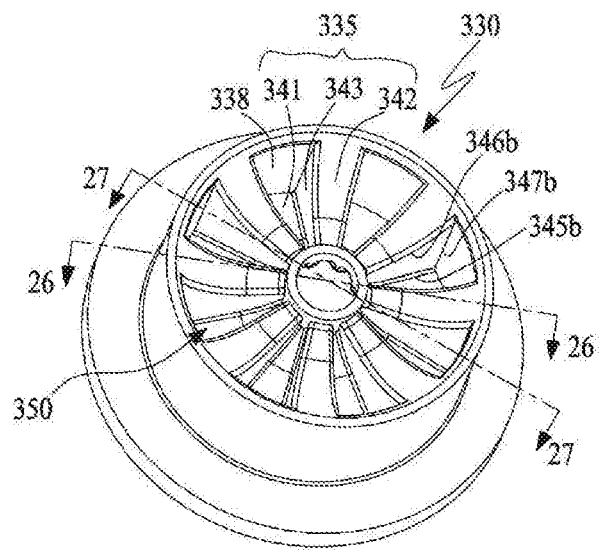
FIG. 25: shows a 3D perspective reverse view of the seal membrane in FIG. 24.
Figure 26:
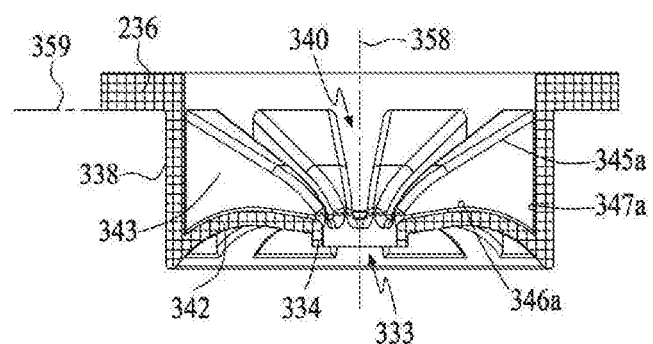
FIG. 26: shows a sectional view along line 26-26 in FIG. 25.
Figure 27:
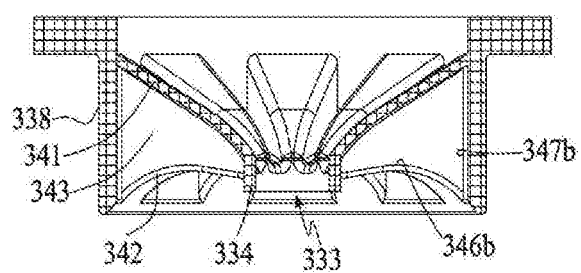
FIG. 27: shows a sectional view along line 27-27 in FIG. 25.

Referring to FIG. 19, when the large diameter instrument is removed out from the seal membrane assembly 180, the seal membrane may be inverted under certain circumstance. In the present embodiment said hooked cantilever 129 blocks the inversion path of the cliff 138; The outer sealing-wall 142 is connected to the cliff 138, which stretches the outer sealing-wall 142 and the outer sealing-wall 142 stretches the sealing lip 134, thereby limiting the depth of the seal inversion, only locally and partially inversion; and effectively reducing the wrapped-area after the inversion. Since said reverse concave-channels have the function of enlarging hoop circumference, and reducing the actual contact area of the two surfaces between the instrument and the seal membrane, the operational comfort of the seal membrane after inversion can be improved to a large extent.

In the present embodiment, the side sealing-walls 143 together reinforce the axial tensile stiffness in the lip-adjacent area; and said side sealing-wall 143 increases the axial tensile stiffness without increasing the hoop stiffness, thus increasing the axial stiffness without increasing the hoop force, such that which can effectively reduce the stick-slip described in the background. In this embodiment, 16 side sealing-walls 143 are included, while more or less side sealing-walls also can increase the axial tensile stiffness.

The channels 140 and the channels 150 can be used to store grease. When a large diameter instrument is inserted, the wrapped-area deformed by said channel is smaller, only a small section of the channels is flattened. The unflattened channels near the wrapped-area have a better function of storing grease. When the instrument moves in the seal membrane, the grease in the wrapped-area is scraped away firstly, and the grease in the unflattened channel adjacent to the wrapped-area will be added to the surface of the instrument, thereby adding to the wrapped-area with the instrument moving. Optionally, the internal width of the channel in the lip-adjacent area is B1, wherein 0.5 mm≤B1≤1 mm. When the inner width of the channel in the lip-adjacent area is smaller than 0.5 mm, the structure of the channel is hard to be manufactured; while the larger the internal width of the channel, the worse the grease storage effect; Researches have shown that when the internal width of the groove is ≤1 mm, the grease storage effect is better. The grease storage of the grooves improves the problem of lubrication unreliability as described in the background, thereby contributing to reduce the stick-slip described in the background.

In summary, the structure of channels has the functions of enlarging hoop circumference, reducing the wrapped-area, reducing the actual contact area of the two surfaces between the instrument and the seal membrane, improving lubrication reliability, increasing the axial tensile stiffness, etc., thereby, the frictional resistance and the stick-slip can be greatly reduced, and the probability of inversion is reduced and the comfort of application is improved.

The lower retaining ring 120 shown in the embodiment is generally circular, but may also be non-circular, or a plurality of parts may be combined by various manners, such as which can be glued, welded, riveted or clamped, or in other mechanical fastening manners. An ordinary skilled can make simple adaptive modifications, such as changing the shape of the hooked cantilever 129, and different shapes of hooks can be achieved to allow the seal membrane to dilate and deform but limit the seal inversion, which does not deviate from the scope of the invention.

FIG. 20-23 show more detailed depiction the seal membrane 230 of the second embodiment in the invention. Said seal membrane 230 includes a distal aperture 233, a sealing lip 234, a sealing wall 235 and a flange 236, said distal aperture 233 formed by the sealing lip 234. As described in the background of the invention, the circumference of the sealing lip should be short and strong enough to ensure sealing reliability when a 5 mm diameter instrument is inserted. In the present embodiment, the sealing lip 234 is circular, defining its radius as Rlip, so that the circumference of the sealing lip is approximately equal to $2*Rlip*\pi$ ($\pi=3.14159$), usually the circumference of the sealing lip is 11.8~43.8 mm. The cross-section of said sealing lip is circular, usually its radius is 0.35 to 0.5 mm diameter.

Said sealing wall 135 connects the sealing lip 134 at one end and the flange 136 at the other end, said seal membrane 230 including the proximal surface and the distal surface. Said sealing lip 234 includes a longitudinal axis 258, and a transverse plane 259 that is approximately perpendicular to the longitudinal axis 258. Said wall 235 including an inner sealing-wall 241, an outer sealing-wall 242 and a side sealing-wall 243. The shape of said inner sealing-wall 241 is a part of semi-sphere. Said inner sealing-wall 241 extends laterally from the sealing lip 234 to the cliff 238; said an outer sealing-wall 242 extends laterally from the sealing lip 234 to said cliff 238; while said cliff 238 and the flange 236 are intersected. The first side of said side sealing-wall 243 intersects the inner sealing-wall 241 and form a line 245a, 245b; the second side of said side sealing-wall 243 intersects the outer sealing-wall 242 to form a line 246a, 246b; the third side of said side sealing-wall 243 intersects said cliff 238 to form a line of intersection 247a, 247b.

Said 2 adjacent side sealing-wall 243 and the outer sealing-wall 242 there between form a channel that is recessed from the proximal surface toward the distal surface and the opening oriented to the proximal surface, which is defined as the normal concave-channel 240; meanwhile, said 2 adjacent side sealing-wall 243 and the inner sealing-wall 241 there between form a channel that is recessed from the distal surface toward the proximal surface and the opening oriented to the distal surface, which is defined as the reverse concave-channel 250. Said inner sealing-wall 241, said side sealing-wall 243 and said outer sealing-wall 242 forms a series of normal concave-channel and reverse concave-channel, and said normal concave-channel and reverse concave-channel alternately distributed around the sealing lip 234, extending laterally outward and gradually increasing in axial depth. That is, a series of channels with the normal and reverse alternately and with the increasing axial depth form a seamless sealing wall 235.

Since the shape of the inner sealing-wall 241 is approximately hemispherical, the second embodiment can make a smaller wrapped-area than the first embodiment when a large diameter instrument is inserted. Similarly, the structure of channels in the second embodiment has the functions of enlarging hoop circumference, reducing the actual contact area of the two surfaces between the instrument and the seal membrane, improving lubrication reliability, increasing the axial tensile stiffness, etc., thereby, the frictional resistance and the stick-slip can be greatly reduced, and the probability of inversion is reduced and the comfort of application is improved.

FIG. 24-27 show more detailed depiction the seal membrane 330 of the third embodiment in the invention. Said seal membrane 330 includes a distal aperture 333, a sealing lip 334, a sealing wall 335 and a flange 336, said distal aperture 333 formed by the sealing lip 334. Said sealing wall 335 connects the sealing lip 334 at one end and connects the flange 336 at the other end, said the seal membrane 330 including the proximal surface and the distal surface. Said sealing lip 334 includes a longitudinal axis 358, and a transverse plane 359 that is perpendicular to the longitudinal axis 358.

Said wall 335 including an inner sealing-wall 341, an outer sealing-wall 342 and a side sealing-wall 343. Said inner sealing-wall 341 extends laterally from the sealing lip 334 to the flange 336; said an outer sealing-wall 342 extends laterally from the sealing lip 334 to said flange 336. The first side of said side sealing-wall 343 intersects the inner sealing-wall 341 and form a line 345a, 345b; the second side of said side sealing-wall 343 intersects the outer sealing-wall 342 to form a line 346a, 346b. The outer sealing-wall 342 has a horizontal-sealing-wall substantially parallel to the transverse plane 359 in the lip-adjacent area; while far from the lip-adjacent area, the outer sealing-wall 342 has an outer curved wall, which recessed from the distal surface toward the proximal surface. That is the center of said outer curved wall is at the distal end.

Said 2 adjacent side sealing-wall 343 and the outer sealing-wall 342 therebetween form a channel that is recessed from the proximal surface toward the distal surface and the opening oriented to the proximal surface, which is defined as the normal concave-channel 340. Meanwhile, said 2 adjacent side sealing-wall 343 and the inner sealing-wall 341 therebetween form a channel that is recessed from the distal surface toward the proximal surface and the opening oriented to the distal surface, which is defined as the reverse concave-channel 350. Said inner sealing-wall 341, said side sealing-wall 343 and said outer sealing-wall 342 forms a series of normal concave-channel and reverse concave-channel, and said normal concave-channel and reverse concave-channel alternately distributed around the sealing lip 334, i.e. a series of channels with the normal and reverse alternately form a seamless sealing wall 335.

Since the outer sealing-wall 241 has an outer curved shape, the present embodiment has better effect of preventing the seal inversion relative to the first embodiment. Similarly, the structure of channels in the second embodiment has the functions of enlarging hoop circumference, reducing the wrapped-area, reducing the actual contact area of the two surfaces between the instrument and the seal membrane, improving lubrication reliability, increasing the axial tensile stiffness, etc., thereby, the frictional resistance and the stick-slip can be greatly reduced, and the probability of inversion is reduced and the comfort of application is improved.

Those skilled in the art easily understand that the reasonable fillet transition can avoid stress concentration or make certain areas deformed more easily. Due to the small size of the seal membrane, especially the area near the sealing lip is smaller, with such a small size and different chamfer, the shape of the seal membrane looks different. In order to clearly show the geometric relationship of the elements, the embodiment of the invention is generally the pattern without the fillet.

Many different embodiments and examples of the invention have been shown and described. One ordinary skilled in the art will be able to make adaptations to the methods and apparatus by appropriate modifications without departing from the scope of the invention. The normal concave-channel and the reverse concave-channel described, in this embodiment cannot be limited to U-shaped or V-shaped. It has been mentioned many times in the invention that the channel extends laterally outward from the sealing lip, and the so-called "extending laterally outward" should not be limited to a straight line. Said "extending laterally outward" can be a spiral, a line segment, a multi-section arc line and so on. In the invention, the positional relationship of the intersecting surfaces composed of said channels and the intersection line thereof are described with reference to specific embodiments, and the methods of increasing curved surfaces to form a multifaceted mosaic or using of the high-order curved surface to make the intersection line and the channel shape to look different from said embodiment. However, it can be considered not deviated from the scope of the invention, as long as it conforms to the general idea of the invention. Several modifications have been mentioned, to those skilled in the art, other modifications are also conceivable. Therefore, the scope of the invention should follow the additional claims, and at the same time, it should not be understood that it is limited by the specification of the structure, material or behavior illustrated and documented in the description and drawings.

I claim:

1. A seal membrane assembly comprising a seal membrane, an upper retainer ring, a lower retainer ring and a protection device; wherein the seal membrane and the protection device are sandwiched between the upper retainer ring and the lower retainer ring;
the lower retainer ring comprises a proximal surface, a distal surface and an annular-shell extending from the proximal surface to the distal surface; the lower retainer ring also includes a plurality of hooked cantilevers connected to the annular-shell and extending from the proximal end to the distal end, and the hooked cantilevers are inserted into a plurality of reverse concave-channels of the seal membrane and are closed to a rotary cliff of the seal membrane;
the seal membrane comprises a proximal opening, a distal aperture, and a sealing wall from the distal aperture extending to the proximal opening; the sealing wall comprises a proximal surface and a distal surface, said distal aperture formed by a sealing lip for accommodating an inserted instrument and forming a gas-tight seal; the sealing wall comprises a plurality of normal concave-channels and the plurality of reverse concave-channels alternately distributed around the sealing lip; and the normal concave-channels are recessed from the proximal surface of the sealing wall toward the distal surface and the opening oriented to the proximal surface; and the reverse concave-channels are recessed from the distal surface of the sealing wall toward the proximal surface and the opening oriented to the distal surface;
the normal concave-channels and the reverse concave-channels extend laterally outward from the sealing lip; the depth of channels gradually increases; and the seal membrane also includes the rotary cliff intersecting the normal concave-channels and reverse concave-channels.

2. The seal membrane assembly according to claim 1, a gap is reserved between the annular-shell of the lower retainer ring and the rotary cliff of the seal membrane to realize the function of allowing diastolic deformation of the cliff and limit the inversion deformation of the seal membrane.

3. The seal membrane assembly of claim 1, wherein an external form of the cliff is approximately cylindrical.

4. The seal membrane assembly of claim 1, wherein complete grooves are formed at intersections of the cliff and the reverse concave-channels, and the cliff prevents a seal inversion.

5. The seal membrane assembly of claim 1, wherein the seal membrane includes a flange intersected with the sealing wall; and an outer floating portion including at least one lateral pleat extends from the flange to the proximal opening.

6. The seal membrane assembly of claim 1, wherein sections of the normal concave-channels and reverse concave-channels are U-shaped.

7. The seal membrane assembly of claim 6, wherein an internal width of the normal concave-channels and reverse concave-channels in the lip-adjacent area is B, and 0.5 mm<B 1 mm.

8. The seal membrane assembly of claim 6, wherein the number of the normal concave-channels and reverse concave-channels is eight.

9. The seal membrane assembly of claim 6, wherein the sealing lip is circular or cylindrical.

10. The seal membrane assembly of claim 6, wherein when a large diameter surgical instrument is inserted into the trocar, an actual contact area of two surfaces between the instrument and the seal membrane is reduced.

11. The seal membrane assembly of claim 1, wherein the sealing wall further comprises a plurality of inner sealing-walls, side sealing-walls and outer sealing-walls; each two side sealing-walls and one outer sealing-wall form a normal concave-channel; and each two side sealing-walls and one inner sealing-wall form a reverse concave-channel.

12. The seal membrane assembly of claim 11, wherein the adjacent normal concave-channel and the reverse concave-channel share a mutual side sealing-wall.

13. The seal membrane assembly of claim 11, wherein the inner sealing-walls deform into an approximately hemispherical shape when a large diameter surgical instrument is inserted.

14. The seal membrane assembly of claim 11, wherein the sealing lip comprises a longitudinal axis and a transverse plane perpendicular to the longitudinal axis; the outer sealing-wall has a horizontal-sealing-wall substantially parallel to the transverse plane in the lip-adjacent area; while far from the lip-adjacent area, the outer sealing-wall has an outer curved wall recessed from the distal surface toward the proximal surface; and a center of the outer curved wall is at the distal end.

15. The seal membrane assembly of claim 11, wherein the thickness of the inner sealing-walls, the side sealing-walls and the outer sealing-walls are substantially uniform.

* * * * *